(12) United States Patent
Wilkins

(10) Patent No.: US 6,416,494 B1
(45) Date of Patent: Jul. 9, 2002

(54) SEMI-COMPLIANT CATHETER BALLOONS AND METHODS OF MANUFACTURE THEREOF

(75) Inventor: Douglas Wilkins, San Jose, CA (US)

(73) Assignee: Infinity Extrusion & Engineering, Inc., Santa Clara, CA (US)

(*) Notice: Subject to any disclaimer, the term of this patent is extended or adjusted under 35 U.S.C. 154(b) by 0 days.

(21) Appl. No.: 09/096,141

(22) Filed: Jun. 11, 1998

(51) Int. Cl.[7] ............................................. A61M 29/00
(52) U.S. Cl. ........................ 604/96.01; 604/103.13; 604/915; 428/35.2
(58) Field of Search ................. 604/96, 915–919, 604/96.01, 103.11, 103.13; 428/35.2

(56) References Cited

U.S. PATENT DOCUMENTS

| | | | |
|---|---|---|---|
| 3,599,620 A | * 8/1971 | Balin | 128/349 B |
| 4,026,296 A | 5/1977 | Stoy et al. | |
| 4,490,421 A | * 12/1984 | Levy | 428/35 |
| 4,861,830 A | * 8/1989 | Ward, Jr. | 525/92 |
| 4,963,313 A | 10/1990 | Noddin et al. | |
| RE33,561 E | 3/1991 | Levy | |
| 5,055,024 A | 10/1991 | Jackowski et al. | |
| 5,270,086 A | 12/1993 | Hamlin | |
| 5,290,306 A | 3/1994 | Trotta et al. | |
| 5,304,340 A | 4/1994 | Downey | |
| 5,344,400 A | 9/1994 | Kaneko et al. | |
| 5,348,538 A | 9/1994 | Wang et al. | |
| 5,403,340 A | 4/1995 | Wang et al. | |
| 5,447,497 A | 9/1995 | Sogard et al. | |
| 5,479,952 A | * 1/1996 | Zachariades et al. | 132/321 |
| 5,531,688 A | * 7/1996 | Hiejima et al. | 604/96 |
| 5,587,125 A | * 12/1996 | Roychowdhury | 264/515 |
| 5,674,930 A | 10/1997 | Sugiura et al. | |
| 5,807,327 A | * 9/1998 | Green et al. | 604/96 |
| 5,810,786 A | * 9/1998 | Jackson et al. | 604/265 |
| 5,833,657 A | * 11/1998 | Reinhardt et al. | 604/96 |
| 5,846,258 A | * 12/1998 | Takayanagi et al. | 606/192 |
| 5,910,533 A | * 6/1999 | Ghosal et al. | 524/560 |
| 6,093,463 A | * 7/2000 | Thakrar | 428/36.9 |

FOREIGN PATENT DOCUMENTS

EP 0362826 4/1990

OTHER PUBLICATIONS

ASTM method D1243–79 as described in "Standard Test Method for Dilute Solution Viscosity of Vinyl Chloride Polymers," pp. 489–492.
Barex barrier resins, Barrier Properties, BP Chemicals.
Barex barrier resins, Barex 210 Extrusion Grade, BP Chemicals, Brochure No.: BX–101 revised 9/91.
Barex barrier resins, Barex 218 Extrusion Grade, BP Chemicals, Brochure No.: BX–102 revised 9/91.
Barex barrier resins, Barex 210—FDA Compliance Direct Food Contact, BP Chemicals.
Barex barrier resins, Source Reduction Guidelines, BP Chemicals, Brochure No.: BX–505 revised 2/93.
Barex barrier resins, application case history, No. 11, BP Chemicals, Jan. 1993.

* cited by examiner

Primary Examiner—Brian L. Casier
Assistant Examiner—Cris L. Rodriguez
(74) Attorney, Agent, or Firm—Medlen & Carroll, LLP

(57) ABSTRACT

The present invention relates to catheter balloons for medical devices. In particular, the present invention provides biaxially oriented semi-compliant catheter balloons comprising acrylonitrile polymers, acrylonitrile copolymers, and acrylonitrile blends, and methods of making same. The catheter balloons provided herein exhibit relatively high tensile strength, controlled compliance, reduced tendency for pinholing, ease of coating with and of bonding to other compounds, as well as resistance to moisture.

47 Claims, 3 Drawing Sheets

SEMI-COMPLIANT CATHETER BALLOONS AND METHODS OF MANUFACTURE THEREOF

FIELD OF THE INVENTION

The present invention relates to catheter balloons for medical devices. In particular, the present invention relates to biaxially oriented semi-compliant catheter balloons comprising acrylonitrile polymers, acrylonitrile copolymers, and acrylonitrile blends. The present invention further comprises methods of making such catheter balloons.

BACKGROUND OF THE INVENTION

Catheter balloons are extensively used in medical applications such as angioplasty, valvuloplasty, urological procedures, and tracheal or gastric intubation. Catheter balloons are generally made using non-compliant materials (e.g., polyethylene terephthalates, polyacrylenesulfide, and copolyesters), compliant materials (e.g., polyvinyl chloride [PVC], polyurethanes, crosslinked low density polyethylenes [PETs], and highly irradiated linear low density polyethylene [LDPE]), or semi-compliant materials (e.g., nylon, and polyamines). Some of the desirable attributes for catheter balloons include high tensile strength (to avoid bursting under pressure and to dilate tough lesions), controlled compliance (to avoid overinflation and subsequent vessel damage), flexibility (to facilitate retraction through vessels), moisture resistance (to avoid loss of mechanical strength), ease of coating with drugs or lubricants, and ease of bonding to a catheter material.

However, no single prior art catheter balloon material offers all of the above-discussed desirable characteristics. For example, while non-compliant balloon materials have the advantage of high tensile strength, this same property makes them resistant to folding and reshapability with the result that they are difficult to retract through vessels. Although decreased wall thickness may overcome folding resistance, it nevertheless results in "pinholing," which is associated with a fragility during insertion and the need for extreme care in handling, as well as possible damage to surrounding tissue caused by high pressure fluid leakage. Additionally, because catheter balloons of non-compliant materials do not inflate beyond a particular distended profile, they cannot be tailored to fit the changing diameter of physiological vessels. Non-compliant materials suffer from the added drawback that they do not readily accept coatings and are difficult to bond to other materials (e.g., catheter materials) due to their higher melt temperatures which resist melting adhesion, and polymer polarity which resists biocompatible adhesives.

Similarly, catheter balloons made of compliant materials exhibit some undesirable characteristics. Compliant balloons are characterized by the ability to continually distend with increasing pressure, thus causing additional distention of the treated vessel. However, this property also risks overinflation of the catheter balloon and subsequent vessel damage. The risk of overinflation is exacerbated by the low tensile strength of compliant materials, which results in balloon burst failure and vessel injury. Though this risk may be reduced by increasing the balloon's wall thickness, the resulting balloons resist folding (i.e., winging) and are more cumbersome to use because of their rigidity.

Catheter balloons which are constructed of art-known semi-compliant materials also possess undesirable properties. For example, while known semi-compliant balloon materials combine the advantages of relatively high tensile strength and controlled compliance, they nevertheless continue to exhibit pinholing, difficulty in coating and bonding with other materials, and excessive material shrinkage. Semi-compliant nylon materials suffer from the additional disadvantage of being hygroscopic, thus suffering from accelerated loss of mechanical strength.

Thus, what is needed is a catheter balloon having relatively high tensile strength, controlled compliance, reduced tendency for pinholing, ease of coating with and of bonding to other compounds, as well as resistance to moisture.

SUMMARY OF THE INVENTION

The invention provides a catheter balloon comprising biaxially oriented acrylonitrile polymer. In one preferred embodiment, the balloon is within its glass transition state at approximately human body temperature. Without intending to limit the invention to a particular wall thickness and tensile strength, in an alternative preferred embodiment, the acrylonitrile polymer catheter balloon has a mean wall thickness of from approximately 0.0006 inches to approximately 0.0013 inches and a tensile strength of at least approximately 15000 psi. While not intending to limit the invention to a particular tailored compliance, in a more preferred embodiment, the tailored compliance of said acrylonitrile polymer catheter balloon is from approximately 5% to approximately 15%. In an alternative embodiment, the acrylonitrile polymer catheter balloon has a mean wall thickness of from approximately 0.0006 inches to approximately 0.0015 inches, reaches approximately quarter size at a pressure from approximately 12 atmospheres to approximately 14 atmospheres, reaches nominal size at a pressure of from approximately 4 atmospheres to approximately 6 atmospheres, and has a rated burst pressure of at least approximately 1 atmosphere greater than said pressure from approximately 12 atmospheres to approximately 14 atmospheres.

The invention further provides a catheter balloon comprising biaxially oriented acrylonitrile copolymer. Without limiting the invention to any particular components, in one embodiment, the acrylonitrile copolymer comprises acrylonitrile and methyl acrylate. Without limiting the invention to any particular components and/or proportions of components, in a preferred embodiment, the acrylonitrile copolymer comprises from approximately 73 to approximately 77 parts by weight of acrylonitrile and from approximately 23 to approximately 27 parts by weight of methyl acrylate, said acrylonitrile copolymer being sold under the trademark "BAREX 210™." In a more preferred embodiment, the BAREX 210™ balloon has a mean wall thickness of from approximately 0.0006 inches to approximately 0.0012 inches and a tensile strength of at least approximately 15000 psi. In yet a more preferred embodiment, the tailored compliance of said acrylonitrile copolymer catheter balloon is from approximately 5% to approximately 15%. In a further preferred embodiment, the intrinsic viscosity of said acrylonitrile copolymer catheter balloon is from approximately 0.8 to approximately 1.3. In yet a further preferred embodiment, the acrylonitrile and methyl acrylate copolymer catheter balloon has a mean wall thickness of from approximately 0.0006 inches to approximately 0.0012 inches, reaches approximately quarter size at a pressure from approximately 12 atmospheres to approximately 14 atmospheres, reaches nominal size at a pressure of from approximately 4 atmospheres to approximately 6 atmospheres, and has a rated burst pressure of at least approximately 1 atmosphere greater than said pressure from approximately 12 atmospheres to approximately 14 atmospheres.

Also without limiting the invention to particular components and/or proportions of components, in an alternative preferred embodiment, the acrylonitrile copolymer comprises from approximately 73 to approximately 77 parts by weight of acrylonitrile and from approximately 23 to approximately 27 parts by weight of methyl acrylate, said acrylonitrile copolymer being sold under the trademark "BAREX 218™." In a more preferred embodiment, the BAREX 218 ™ catheter balloon has a mean wall thickness of from approximately 0.0006 inches to approximately 0.0013 inches and a tensile strength of at least approximately 15000 psi. In yet a more preferred embodiment, the tailored compliance of said acrylonitrile copolymer catheter balloon is from approximately 5% to approximately 15%. In a further preferred embodiment, the intrinsic viscosity of said acrylonitrile copolymer catheter balloon is from approximately 0.8 to approximately 1.3. In yet a further preferred embodiment, the BAREX 218™ catheter balloon has a mean wall thickness of from approximately 0.0006 inches to approximately 0.0013 inches, reaches approximately quarter size at a pressure from approximately 12 atmospheres to approximately 14 atmospheres, reaches nominal size at a pressure of from approximately 4 atmospheres to approximately 6 atmospheres, and has a rated burst pressure of at least approximately 1 atmosphere greater than said pressure from approximately 12 atmospheres to approximately 14 atmospheres.

Also provided by the invention is a catheter balloon comprising biaxially oriented acrylonitrile blend. Without limiting the invention to any particular components, in one embodiment, the acrylonitrile blend comprises acrylonitrile and polyethylene elastomer. Without intending to limit the invention to any particular proportion of components, in a preferred embodiment, the acrylonitrile blend comprises approximately 70 parts by weight of acrylonitrile and approximately 30 parts by weight of polyethylene elastomer. In a more preferred embodiment, the polyethylene elastomer catheter balloon has a mean wall thickness of from approximately 0.00065 inches to approximately 0.0015 inches and a tensile strength of at least approximately 15000 psi. In yet a more preferred embodiment, the tailored compliance of said acrylonitrile blend catheter balloon is from approximately 5% to approximately 15%. In a further preferred embodiment, the intrinsic viscosity of said acrylonitrile blend catheter balloon is from approximately 0.8 to approximately 1.3. In yet a further preferred embodiment, the acrylonitrile and polyethylene elastomer blend catheter balloon has a mean wall thickness of from approximately 0.0006 inches to approximately 0.0012 inches, reaches approximately quarter size at a pressure from approximately 12 atmospheres to approximately 14 atmospheres, reaches nominal size at a pressure of from approximately 4 atmospheres to approximately 6 atmospheres, and has a rated burst pressure of at least approximately 1 atmosphere greater than said pressure from approximately 12 atmospheres to approximately 14 atmospheres.

Also without limiting the invention to any particular components, in an alternative embodiment, the acrylonitrile blend comprises acrylonitrile and a block copolymer comprising crystalline polybutylene terephthalate and amorphous long chain glycols, said block copolymer being sold under the trademark "HYTREL™." While not intending to limit the invention to any particular proportion of components, in a preferred embodiment, the acrylonitrile blend comprises approximately 70 parts by weight of acrylonitrile and approximately 30 parts by weight of HYTREL™. In a more preferred embodiment, the acrylonitrile and HYTREL™ blend catheter balloon has a mean wall thickness of from approximately 0.0006 inches to approximately 0.0013 inches and a tensile strength of at least approximately 15000 psi. In yet a more preferred embodiment, the tailored compliance of said acrylonitrile blend catheter balloon is from approximately 5% to approximately 15%. In a further preferred embodiment, the intrinsic viscosity of said acrylonitrile blend catheter balloon is from approximately 0.8 to approximately 1.3. In yet a further preferred embodiment, the acrylonitrile and HYTREL™ blend catheter balloon has a mean wall thickness of from approximately 0.0006 inches to approximately 0.0013 inches, reaches approximately quarter size at a pressure from approximately 12 atmospheres to approximately 14 atmospheres, reaches nominal size at a pressure of from approximately 4 atmospheres to approximately 6 atmospheres, and has a rated burst pressure of at least approximately 1 atmosphere greater than said pressure from approximately 12 atmospheres to approximately 14 atmospheres.

Without limiting the invention to any components, in another alternative embodiment, the acrylonitrile blend comprises acrylonitrile and polyether block amide. In a preferred embodiment, the acrylonitrile blend comprises approximately 60 parts by weight of acrylonitrile and approximately 40 parts by weight of polyether block amide. In a more preferred embodiment, the acrylonitrile and polyether block amide blend catheter balloon has a mean wall thickness of from approximately 0.0006 inches to approximately 0.0013 inches and a tensile strength of at least approximately 15000 psi. In yet a more preferred embodiment, the tailored compliance of said acrylonitrile blend catheter balloon is from approximately 5% to approximately 15%. In a further preferred embodiment, the intrinsic viscosity of said acrylonitrile blend catheter balloon is from approximately 0.8 to approximately 1.3. In yet a further preferred embodiment, the acrylonitrile and polyether block amide blend catheter balloon has a mean wall thickness of from approximately 0.0006 inches to approximately 0.0013 inches, reaches approximately quarter size at a pressure from approximately 12 atmospheres to approximately 14 atmospheres,. reaches nominal size at a pressure of from approximately 4 atmospheres to approximately 6 atmospheres, and has a rated. burst pressure of at least approximately 1 atmosphere greater than said pressure from approximately 12 atmospheres to approximately 14 atmospheres.

The invention additionally provides methods for making biaxially oriented catheter balloons, comprising: a) providing a material selected from the group consisting of acrylonitrile, acrylonitrile copolymer, and acrylonitrile blend; b) extruding said material to form an extruded tube; c) heat setting said extruded tube to form a heat set tube; d) longitudinally drawing said heat set tube to form a drawn tube; e) radially expanding said drawn tube to form a balloon member; and f) heat setting said balloon member to form a heat set balloon member. Without limiting the means and/or temperature of extrusion, in one embodiment, extruding is performed in a die comprising a barrel zone, and wherein said die is at a temperature of from approximately 500° F. to approximately 560° F. and said barrel zone is at a temperature of from approximately 400° F. to approximately 470° F. In a preferred embodiment, the method further comprises after step b), quenching said extruded tube in a water bath at approximately 22° C. In a more preferred embodiment, the distance between said water bath and said die is from approximately 0.2 inches to approximately 1.0 inches.

In an alternative embodiment, the tube is extruded at a drawdown ratio of less than 3:1. In a preferred embodiment, the drawdown ratio is approximately 2:1.

In another alternative embodiment, the heat setting is at a temperature of from approximately 60° C. to approximately 80° C.

In yet another alternative embodiment, the heat setting is for a period of at least approximately two hours.

In a further alternative embodiment, the time between said heat setting and said extruding is less than approximately eight hours.

In another alternative embodiment, the drawing is at a tube draw temperature between the first order glass transition temperature and the second order glass transition temperature of said material. In a preferred embodiment, the tube draw temperature is from approximately 300° C. to approximately 450° C. In an alternative preferred embodiment, the length of said drawn tube is from approximately 2 times to approximately 5 times the length of said extruded tube.

In a further alterative embodiment, the radially expanding is at a blow up ratio of from approximately 5.25:1 to approximately 7.25:1.

In yet another alternative embodiment, the ratio of mean wall thickness of said heat set tube to said heat set balloon is from approximately 15:1 to approximately 20:1.

In another alternative embodiment, the heat setting of said balloon member comprises raising the temperature of said balloon member to a heat setting temperature greater than the glass transition temperature of said material to form a heated balloon member, followed by cooling said heated balloon member to a temperature below the glass transition temperature of said material. In one preferred embodiment, the heat setting temperature is from approximately 90° C. to approximately 180° C. In another preferred embodiment, the glass transition temperature is from approximately 180° C. to approximately 240° C. In yet another preferred embodiment, the temperature below the glass transition temperature is from approximately 20° C. to approximately 25° C.

DEFINITIONS

Figure 1:
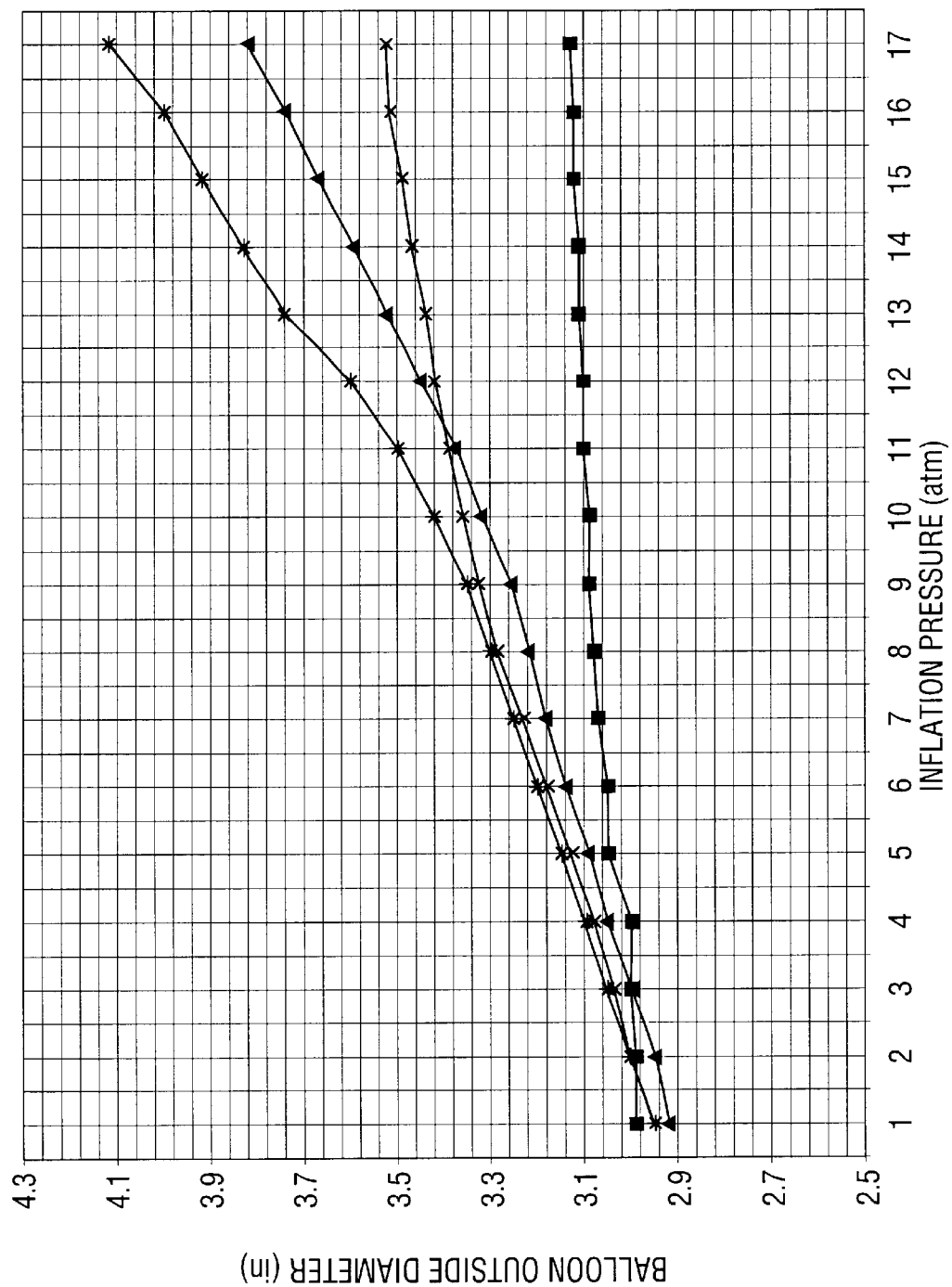
FIG. 1 shows the change in the outside diameter, in response to pressure, of 3.0 mm balloons fabricated of polyacrylonitrile (x), nylon (Δ), highly irradiated linear low density polyethylene (LDPE) (*), and crosslinked low density polyethylene (PET) blend (■).

To facilitate understanding of the invention, a number of terms are defined below.

The term "single layer" when made in reference to a catheter balloon refers to a catheter balloon composed of only one layer.

The terms "catheter balloon" and "balloon" as used herein refer to an inflatable portion of a tubing.

As used herein, the term "biaxially oriented" when made in reference to a material refers to a material which, while in a solid state, has been subjected to expansion forces that are applied both parallel to and radially from an axis of a structure containing the material. For example, a catheter balloon structure comprising biaxially oriented polymer refers to a catheter balloon wherein the polymer which is contained in, for example, a tubing, which has been drawn while in a solid state in essentially the same direction as the tubing's longitudinal axis and also radially expanded in a direction which is essentially perpendicular to the tubing's longitudinal axis. The term "biaxially oriented material" does not include compositions which are extruded while in other than solid state (e.g., in a liquid or in a gel state).

A "polymer" refers to a composition in which two or more molecules of the same or different compound are covalently linked. A polymer may be a homopolymer or a heteropolymer. A "homopolymer" is a polymer of the molecules of one compound. For example, the terms "acrylonitrile homopolymer" and "polyacrylonitrile" refer to a polymer of acrylonitrile molecules. A "heteropolymer" (also referred to as "copolymer") is a polymer of the molecules of more than one compound. For example, "acrylonitrile copolymer" refers to a polymer of acrylonitrile molecules with other than acrylonitrile molecules.

The term "blend" when made in reference to two or more compounds refers to a composition in which the two or more compounds are physically mixed together in the absence of covalent bonding between the two compounds.

The term "intrinsic viscosity" refers to the viscosity of a material as determined at 25° C. as determined by the ASTM method D1243-79 as described in "Standard Test Method for Dilute Solution Viscosity of Vinyl Chloride Polymers," copies of which may be obtained from the American Society for Testing Materials, 1916 Race St., Philadelphia, Pa. 19103, or examined at the Office of the Federal Register, 1100 L St. NW., Washington, D.C. 20408.

The terms "compliance" and "tailored compliance" are used interchangeably herein in reference to a tubing or a balloon and refer to the change in the mean outer diameter of the tubing or balloon, respectively, per unit atmospheric pressure applied radially to the inner surface of the tubing or balloon, respectively. For example, a balloon having a tailored compliance of 13% at a pressure of 10 atmospheres refers to a balloon whose mean outside diameter at 10 atmospheres is 13% greater than the mean outside diameter of the balloon at 9 atmospheres. The term "controlled compliance" when made in reference to a balloon means a balloon which exhibits substantially uniform distension in response to increasing pressure.

The terms "burst pressure," "tensile strength," and "burst strength" in reference to a balloon refer to the pressure at ambient temperature (about 20° C.) which is applied to the inner wall of the balloon and at which the balloon ruptures. Burst pressure of a balloon may be determined by sealing off one end of the balloon and introducing a fluid (e.g., liquid or gas) into the other end at incrementally increasing fluid pressure and determining the fluid pressure at which the balloon bursts. The term "average burst pressure" refers to the average of the burst pressure of a number of balloons. The term "rated burst pressure" is the pressure at which a balloon bursts with from a 95% to a 99% probability. Rated burst pressure may be calculated as follows:

$$\text{Rated Burst Pressure} = \text{Average Burst Pressure} - (\text{Standard Deviation} \times K \text{ Factor}),$$

where K Factor is a statistical factor based upon the number of samples tested. The term "high tensile strength" refers to the range of tensile strength values exhibited by non-compliant catheter balloons.

The term "drawdown ratio" when made in reference to a parison which is extruded to form a tubing refers to the ratio of the length of the tubing to the length of the parison. For example, a drawdown ratio of 3:1 means that the length of the tubing is three times the length of the parison from which it was extruded.

The terms "expansion ratio" and "blow up ratio" are used interchangeably herein to refer to the ratio of the mean inner diameter of a tubing to the mean inner diameter of a balloon expanded from the tubing. For example, radially expanding a tubing having a mean inner diameter of 0.018 inches at a blow up ratio of 6.5 yields a balloon with a mean inner diameter of 0.117 inches.

The terms "tubing draw" and "tubing stretch length" where used herein in reference to a drawn tubing which is drawn from a formed tubing refer to the fold increase in the length of the drawn tubing as compared to the length of the formed tubing. For example, a tubing draw value of 5 is obtained when a formed tubing, which has a length Li, is stretched to make a drawn tubing of length L2, where L2 equals 5 (five) times Li.

The terms "tubing draw temperature" and "tubing stretch temperature" are used interchangeably herein to refer to the mean temperature at which a tubing is drawn or stretched essentially along its longitudinal axis.

The term "first order glass transition temperature" refers to the temperature at which a compound (e.g, polymer) exhibits transition from a solid state to a rubber state.

The terms "second order glass transition temperature" and "flow temperature" interchangeably refer to the temperature at which a compound (e.g., polymer) exhibits transition from a rubber state to a liquid state.

The term "glass transition state" refers to the state at which an amorphous compound (e.g., polymer) becomes transparent and glass-like. Typically, molecular movement other than bond vibrations in the compound is limited while in the glass transition state.

The term "approximately" when made in reference to a value refers to a range of values which is equal to the value ±10%, more preferably ±5%. For example, tensile strength of at least approximately 15000 psi refers to a range of tensile strengths from 13500 psi to 16500 psi, more preferably from 14250 psi to 15750 psi.

The term "non-distended" when made in reference to a catheter balloon refers to a catheter balloon which is not subjected to radial pressure which is applied to the balloon's inner surface that is greater than atmospheric pressure. Non-distended catheter balloons include, for example, a catheter balloon which does not contain a fluid, or which contains a fluid that is not under pressure. In contrast, the term "distended" when made in reference to a catheter balloon refers to a catheter balloon which has been or is being subjected to radial pressure applied to the balloon's inner surface that is greater than atmospheric pressure, such as that exerted by a pressurized fluid (e.g, liquid or gas) contained within the catheter balloon.

The term "non-compliant" when made in reference to a catheter balloon refers to a balloon which does not inflate beyond a particular distended profile. Non-compliant balloons are exemplified by those fabricated out of polyethylene terephthalates, polyacrylenesulfide, and copolyesters.

The term "compliant" when in reference to a balloon means a balloon which continually distends with increasing pressure. Typically, though not necessarily, compliant balloons also have lower tensile strength compared to the tensile strength of a non-compliant balloon of the same dimensions. Compliant balloons are illustrated by those made of, for example, polyvinyl chloride (PVC), polyurethanes, crosslinked low density polyethylenes (PETs), and highly irradiated linear low density polyethylene (LDPE).

The term "semi-compliant" as used herein in reference to a catheter balloon refers to a balloon which continually distends with increasing pressure and which has a tensile strength which is greater than the tensile strength of a compliant balloon of the same dimensions. Semi-compliant balloons are exemplified by, but not limited to, balloons made of nylon and polyamines.

The term "BAREX™" refers to a trademarked acrylonitrile methylacrylate copolymer resin which is sold by BP Chemicals (Cleveland Ohio) and which contains different proportions of acrylonitrile and methylacrylate. For example, BAREX 210™ refers to an acrylonitrile methylacrylate copolymer resin which is formed by copolymerization of 73–77 parts by weight of acrylonitrile and 23–27 parts by weight of methyl acrylate in the presence of 8–10 parts by weight of butadiene-acrylonitrile copolymers containing approximately 70% by weight of polymer units derived from butadiene. "BAREX 218™" refers to an acrylonitrile methylacrylate copolymer resin which is formed by copolymerization of 75–77 parts by weight of acrylonitrile and 23–25 parts by weight of methyl acrylate in the presence of 15–20 parts by weight of butadiene-acrylonitrile copolymers containing approximately 75% by weight of polymer units derived from butadiene.

The term "LOPOC™" refers to a trademarked acrylonitrile styrene acrylate (ASA) copolymer containing 66–72 parts acrylonitrile and 28–34 parts styrene.

The term "HYTREL™" refers to a trademarked block copolymer, containing a hard (i.e., crystalline) segment of polybutylene terephthalate and a soft (i.e., amorphous) segment of long chain glycols. "HYTREL" is supplied as cylindrical pellets and manufactured by DuPont Polymers (Wilmington, Del.).

DESCRIPTION OF THE INVENTION

The invention provides semi-compliant catheter balloons which exhibit a unique combination of high tensile strength and controlled compliance. This combination of properties make the balloons provided herein particularly useful for applications where predictable compliance at given pressures in combination with high tensile strength is desirable (e.g., for use as stents in blood vessels). Furthermore, the semi-compliant balloons of the invention have a reduced tendency for pinholing as compared with semi-compliant nylon catheter balloons, and are readily coated with and bonded to other compounds.

Additionally, the catheter balloons provided herein provide the advantage of resistance to moisture. This limits the degradation of the mechanical properties (e.g., compliance and tensile strength) of the balloon as compared to balloons made of nylon or polyamide. Importantly, the moisture barrier properties of the balloons permit sterilization of the balloons by ethylene oxide gas sterilization (ETO) and radiation without loss of the balloons desirable mechanical properties.

Moreover, while the balloons of the invention have a higher tensile strength than compliant balloons of similar dimensions, they are nevertheless softer than such balloons. The softness of the balloons provided herein makes them easier to handle.

The balloons of the invention may be used in, for example, surgical devices to be introduced into cavities of a living body, such as a catheter, intubation or sounding tubing, cystoscope, or the like. For example, where the balloons of the invention are used in a surgical catheter, a catheter tubing (to which the balloon is fused) is introduced into the vascular system, typically with the aid of a guiding catheter, until the balloon is located at an occlusion site (e.g., site of a stenosis). At this stage the balloon is typically folded and collapsed. A pressurized fluid is inserted at the proximal end of the catheter tubing for inflation of the balloon. The pressure of the fluid unfolds the balloon until it presents a relatively smooth outer surface for imparting forces that are radially outwardly directed at the desired site within the body in order to achieve the desired result of lesion dilation, occlusion reduction or similar treatment.

In one embodiment, the catheter balloons of the invention are contemplated to comprise acrylonitrile homopolymer. In another embodiment, the balloons provided herein are intended to include acrylonitrile copolymers, such as those exemplified by acrylonitrile and methyl acrylate copolymers (e.g., BAREX 210™ and BAREX 218™) and by acrylonitrile styrene acrylate (ASA) copolymers (e.g., LOPOC™). In yet another embodiment, the invention's balloons are contemplated to include acrylonitrile blends (e.g., a blend of acrylonitrile with one or more of polyethylene elastomer, polybutylene terephthlate (PBT), polyether block amide, nylon, HYTREL™, and polyethylene naphthalate (PEN).

The semi-compliant balloons of the invention are fabricated by biaxially orienting a tubing which is extruded out of a desired material while manipulating the extrusion drawdown ratio, blow up ratio, the temperature at which the extruded tubing is heat set, the tubing draw, and the tubing draw temperature. More specifically, if the desired material is a polymer or blend, polymerization and blending, respectively, are initially performed. The polymerized or blended material preferably has a density (as determined by ASNI/ASTM D1505) of from about 0.8 g/cm$^3$ to about 1.45 g/cm$^3$, and more preferably from about 0.95 g/cm$^3$ to about 1.35 g/cm$^3$. The polymerized or blended material is then dried (e.g., in a desiccant hopper dryer), preferably at from about 150° F. to about 300° F., more preferably at from about 175° F. to about 275° F., and most preferably at from about 200° F. to about 240° F. for a minimum of 4 hours, and ground to a fine powder. The powder is extruded under conditions such that the difference in the temperature of the die and zone is from about 20° F. to about 170° F., more preferably from about 25° F. to about 165° F., and yet more preferably from about 30° F. to about 160° F. While not intending to limit the range of die temperature and zone temperature at which the powder is extruded, in one preferred embodiment, the die temperature is maintained from about 500° F. to about 560° F., while the barrel zone temperature is maintained at from about 400° F. to about 470° F. This temperature profile minimizes both extrudate degradation as well as tubing crystallinity.

The extrudate is quenched in a water bath at approximately room temperature (about 22° C.). The distance between the water bath and the die is maintained preferably at from about 0.4 inches to about 0.8 inches, more preferably from about 0.3 inches to about 0.7 inches, and most preferably at from about 0.2 inches to about 0.6 inches. This distance allows a quicker quench than if the distance were increased, and thus results in a more amorphous and less crystalline extruded material. The inventors have observed that as the distance between the water bath and the die was increased, the crystallinity of the extruded tubing material increased, thus resulting in a balloon with higher burst strength and lower compliance as compared to a balloon formed from a tubing which was extruded using a smaller bath-to-die distance. This finding was surprising because it was in direct contradiction to the art-accepted changes in the molecular structure of prior-art balloon materials (e.g., nylon, polyester, polyethylene, etc.) in response to extrusion cooling conditions (See e.g., John J. Aklonis and William J. MacKnight, "*Introduction to Polymer Viscoelasticity*," John Wiley & Sons [1983]).

In order to produce a balloon with semi-compliant properties, the sizes of the extrusion die and mandrel are selected to provide a drawdown ratio equal to or less than 3:1, more preferably equal to or less than 2.5:1 and most preferably equal to about 2:1. A drawdown. ratio greater than 3:1, while yielding a balloon of high burst strength due to the increased longitudinal orientation, also results in a lowered compliance, increased stiffness, and radial bursting as a consequence of the greater tensile strength.

The size of the extruded tubing is manipulated such that it provides a blow up ratio of from about 4.5:1 to about 7.5:1, more preferably between from about 5.25:1 to about 7.25:1. Blow up ratios that are less than 5.25:1 yield balloons which are of higher compliance and lower burst strength than the compliance and burst strength of balloons obtained from tubing at a blow up ratio of equal to or greater than 5.25:1. On the other hand, blow up ratios which are greater than 7.25:1 yield balloons with a lower compliance and higher burst strength than the compliance and burst strength of those balloons which are produced from tubing that is expanded at a blow up ratio of equal to or less than 7.25:1.

The size of the extruded tubing is also manipulated such that the wall thickness of the tubing is from about 10-fold to about 25-fold, more preferably from about 12-fold to about 23-fold, and most preferably from about 15-fold to about 20-fold the wall thickness of the balloon. The thickness of the tubing is also manipulated such that the mean inner diameter of the tubing is from about two-third (⅔)-fold to about quarter (¼) times the mean outer diameter of the tubing.

Once a tubing of the desired dimensions is extruded, the tubing is preferably heat set. Heat setting allows the final stages of crystallization to occur, and minimizes shrinkage of the resulting balloon following heat sterilization. Additionally, heat setting the tubing prior to blowing the balloon results in a softer balloon as compared to a balloon which is inflated from a tubing that had not been heat set. Where heat setting is desirable, it is performed preferably within about 8 hours after extrusion, and preferably for a minimum period of about 2 hours. It is also preferred that heat setting is carried out at from about 50° C. to about 90° C., more preferably from about 55° C. to about 85 ° C., and most preferably from about 60° C. to about 80° C.

The heat set tubing is uniformly stretched along its longitudinal axis (e.g., by applying tension manually, mechanically, by gravity, by weights, or by drawing a length of tubing through a sizing die) to a tubing stretch length of preferably from about 2 times to about 5 times the length of the heat set tubing. Stretching is performed at a tubing stretch temperature between the first order and the second order transition temperatures of the material of the tubing, preferably at from about 250° F. to about 500° F., more preferably from about 275° F. to about 475° F., and most preferably from about 300° F. to about 450° F. Heating may be achieved, for example, under a heat nozzle, in a chamber, or through a die or mold. The drawn tubing is then cooled to room temperature under a flow of air.

The drawn section of the tubing is placed into a balloon molding apparatus which provides uniform heating. Apparatuses for balloon molding which achieve longitudinal stretching, biaxial orientation, heating and cooling are known in the art. These apparatuses also include means for monitoring radial expansion or biaxial orientation, all of which can be conveniently controlled by suitable means such as hard circuitry, a microprocessor, or other computerized controlling arrangements. Thus, these various parameters may be precisely set and readily modified in order to manipulate the conditions for fabricating a particular tubing into a balloon having a specified sizing. The balloon mold may be made from metal or glass and may be heated by cartridge heaters, a heated liquid, a heat nozzle, a heated block or the like. Balloon molds of different configurations allow the formation of a variety of balloon shapes, (e.g., containing expansion knurls, ridges, beads, and ribs) to assist in the folding of the balloon on the final product.

The drawn section of the tubing is biaxially oriented by expanding a portion of the tubing radially and thereby delineating a balloon portion. Biaxial orientation is carried out by exerting pressure on the inside wall of the tubing using a pressurized fluid, such as a gas (e.g., compound air, nitrogen, argon, etc.) or liquid (e.g, water, alcohol, etc.). For example, the tubing may be positioned at a distal taper section of the balloon mold to provide for a low profile distal taper and thinned distal adaption end. The distal end of the drawn tubing is clamped or pinched outside the mold, while the undrawn section of the tubing is supplied with a pressure source (e.g. nitrogen or air under a pressure of from about 50 psi to about 300 psi, more preferably from about 100 psi to about 200 psi). Tension is then applied to the tubing (e.g., by pinch clamps on each side of the mold, in order to maintain, increase or decrease balloon wall thickness). Tension may be supplied, for example, manually or mechanically by weights or under gravity. The mold containing the tubing is then uniformly heated by placement into a heated chamber, cylinder or nozzle. Alternatively, the tubing may be maintained in a stationary position while rotating a heated mold around or over it. The mold temperature is maintained from about 250° F. to about 500° F., more preferably from about 300° F. to about 450° F., and most preferably from about 320° F. to about 420° F. A balloon which is blown within this range of pressures and temperatures is expected to have a blow up ratio of from about 3 to about 5.

While still in the distended state in the mold, the balloon is then heated (e.g., by nozzle, chamber or cylinder) to set the expanded dimensions thereof. The heat setting temperature varies with the type of material used, the wall thickness of the balloon and the heat treatment time. For example, the heat setting temperature for a acrylonitrile homopolymer balloon with a 0.001 inch wall thickness is from about 150° F. to about 400° F., more preferably from about 200° F. to about 350° F., and most preferably from about 220° F. to about 320° F. Heat setting is desirable since it increases biaxial orientation, crystallinity, and compliance of the balloon as compared to a balloon which is not heat set. The heat set balloon will retain its form and about 95% of its mean expanded outside diameter upon being cooled. If the balloon is not heat set, it will shrink back to from about 40% to about 50% of the mean outside diameter to which it had been biaxially oriented in the mold.

The balloon is then cooled using pressurized fluid, such as a gas (e.g., compound air, nitrogen, argon, etc.) or liquid (e.g., water, alcohol, etc.), to a temperature which is below the balloon material's second order transition temperature. The balloon is then removed from the mold by disconnecting the pressure source and applying a vacuum to the balloon to help physically remove the balloon from the mold.

The catheter balloons of the invention are bondable to catheters by, for example, adhesives (e.g., epoxy adhesives, urethane adhesives, and cyanoacrylates), hot melt bonding, ultrasonic welding, heat fusion and the like. Furthermore, the balloons provided herein may also be attached to the catheter by mechanical means such as swage locks, crimp fittings, threads and the like.

The catheter balloons provided herein may be coated with pharmaceutical compounds (e.g., heparin), and non-thrombogenic lubricants (e.g., polyvinyl pyrrolidone). Additionally, the balloons of the invention may be filled with radiopaque media (e.g., barium sulfate), bismuth subcarbonate, iodine containing molecules, tungsten, plasticizers, extrusion lubricants, pigments, antioxidants and the like.

EXPERIMENTAL

The following examples serve to illustrate certain preferred embodiments and aspects of the present invention and are not to be construed as limiting the scope thereof.

In the experimental disclosure which follows, the following abbreviations apply:

EXAMPLE 1

Preparation of Biaxially Oriented Balloons Of Acrylonitrile Polymer, BAREX 210™, Acrylonitrile/HYTREL™ Blend, And BAREX™/HYTREL™ Blend The following experiment was conducted in order to prepare catheter balloons with a mean 3.0 mm outside diameter and a wall thickness of 0.0007–0.0008 inches using acrylonitrile polymer, BAREX 21™, acrylonitrile/HYTREL™ 70/30 blend (i.e., containing 70 parts by weight of acrylonitrile and 30 parts by weight of HYTREL™), and BAREX™/HYTREL™ 60/40 blend (i.e., containing 60 parts by weight of BAREX 210™ and 40 parts by weight of HYTREL™).

For polyacrylonitrile balloons, polyacrylonitrile with an average degree of polymerization of 98% was used. For BAREX 210™ balloons, BAREX 210™ resin (BP Chemicals) was used. For acrylonitrile/HYTREL™ blend balloons, acrylonitrile with an average degree of polymerization 98% was blended with HYTREL™ pellets (DuPont) at the desired weight ratios shown in Table 1 prior to drying. For BAREX™/HYTREL™ balloons, BAREX 210™ resin and HYTREL™ resin were blended at the ratios shown in Table 1.

Each of the blended or polymerized starting materials was dried in a desiccant hopper dryer at 200–240° F. for 4 hours and pelletized or tumble mixed into a substantially uniform resin. Table 1 shows the conditions for extruding tubing and for blowing balloons using the above-described starting materials. These measurements were for 3.00 mm balloon tubing and are considered nominal for all sizes.

TABLE 1

Conditions For Manufacturing Balloons Using Polyarylonitrile, BAREX 210 ™ Acrylonitrile/HYTREL ™, and BAREX 210 ™ /HYTREL ™

| Material | Zone 1 (° F.) | Zone 2 (° F.) | Zone 3 (° F.) | Zone 4 (° F.) | Adapter Temp. (° F.) | Die (° F.) | Drawdown Ratio | Tubing Size (inches)[1] | Blowup Ratio | Balloon Wall Thickness (inches) | Tube Set Temp (° C.) | Blow Temp (° F.) | Blow Pressure (psi) | Balloon Heat Set Temp (° F.) |
|---|---|---|---|---|---|---|---|---|---|---|---|---|---|---|
| Acrylonitrile | 410 | 430 | 450 | 470 | 520 | 550 | 2 to 1 | .020/.043 | 5.9 | 0.0007 | 60 | 420 | 190 | 300 |
| BAREX ™ | 400 | 410 | 425 | 425 | 460 | 460 | 2 to 1 | 0.20/.043 | 5.9 | 0.00075 | 60 | 420 | 190 | 300 |
| ACR/ HYTREL ™ Blend (70/30) | 400 | 420 | 440 | 460 | 525 | 560 | 2.25 to 1 | .019/.045 | 6.2 | 0.00075 | 60 | 410 | 185 | 280 |
| BAREX ™ / HYTREL ™ Blend (60/40) | 400 | 410 | 420 | 435 | 470 | 490 | 2.25 to 1 | .019/.045 | 6.2 | 0.0008 | 65 | 400 | 180 | 280 |
| Tolerances | 10 | 10 | 10 | 10 | 10 | 10 | n/a | +/−.001" | n/a | +/−.0001 | +/−5 | +/−10 | +/−10 | +/−10 F |

[1]Ratio of inside diameter to outside diameter of extruded tubing.

The pelletized starting material was extruded in a single screw thermoplastic extruder (Davis Standard, 1" Machine) at a die temperature of 460–525° F. and a barrel zone temperature of 400–470° F. (Table 1). The temperature in Zones 1–4 shown in Table 1 represent the temperature in the four heat zones along the machine up to the Adapter zone which holds the cross head die onto the machine. The drawdown ratios for the different materials ranged from 2:1 to 2.5:1 as shown in Table 1. The tubing was extruded to a mean inner diameter of from 0.019 inches to 0.020 inches (i.e., blow up ratio of 5.9 to 6.2). The extrudate was quenched in a water bath at room temperature (about 22° C.) with the distance between the water bath and the die maintained at 0.4 inches.

The tubing was heat set within two hours after extrusion at 60–65° C. Heat setting was for two hours prior to balloon blowing. The heat set tubing was uniformly heat drawn with tension at 400–420° F. to a length which was 2–5 times the length of the heat set tubing and a mean inside diameter of which was ¼–¾ times the mean inside diameter of the heat set tubing. The drawn tubing was cooled to room temperature under a flow of air.

The drawn section of the tubing was placed into a glass or metal balloon mold and positioned at the distal taper section of the mold to provide for a low profile distal taper and thinned distal adaption end. The distal end of the drawn tubing was clamped off outside the mold, while the undrawn section of the tubing was supplied with nitrogen under a pressure of 180–190 psi. Tension was then applied to the tubing by pinch clamps on each side of the mold, and the mold was heated and maintained at 400–420° F. While still in the distended state in the mold, the balloon was heat set at a temperature of 280–320° F. using a heated pressurized transversing nozzle. The balloon was cooled to room temperature using cool air or fluid prior to removing it from the mold by disconnecting the pressure source and applying a vacuum to the balloon.

The above-described step resulted in the production of catheter balloons with a 3.0 mm mean outside diameter and 0.0006–0.0013 inch wall thickness as shown in Table 1. The optimized parameters (except tubing size) shown in Table 1 were also optimal or near-optimal for any other balloon size of the respective material (data not shown).

EXAMPLE 2

Physical Properties Resins And Catheter Balloons

This experiment was carried out in order to compare the physical properties of resins and balloons made of polyacrylonitrile, BAREX 210™, and HYTREL™, and of non-compliant nylon balloons and semi-compliant crosslinked low density polyethylene (PET) balloons.

Catheter balloons with a 3.0 mm mean outside diameter and mean wall thickness of 0.0007 inches were prepared using polyacrylonitrile, BAREX 210™, HYTREL™, and BAREX™/HYTREL™ (70/30 by weight) using the conditions described in Example 1. In addition, 3.0 mm×20 mm polyethylene balloons (Guidant PE600) and nylon balloons (Johnson and Johnson/Cordis Duralyn) were also used.

The tensile strength, hardness and percentage elongation of the resins and balloons were compared. The results are shown in Table 2.

TABLE 2

Comparison Of Physical Properties Of Resins And Balloons

| Material | Tensile Strength-Yield (Psi) | Hardness (D) | Elongation (%)[1] |
|---|---|---|---|
| BAREX ™ Resin | 9500 LB/IN2 | M60 | 3.50% |
| Acrylonitrile Resin | 9000 LB/IN2 | M75 | 3.50% |
| HYTREL ™ Resin | 4000 LB/IN2 | D82 | 400% |
| Acrylonitrile Balloon | 18600 LB/IN2 | M67 | 3.00% |
| BAREX ™ Balloon | 20000 LB/IN2 | M50 | 3.00% |
| HYTREL ™ Balloon | 4000 LB/IN2 | D76 | 375% |
| BAREX ™/ HYTREL ™ Balloon | 22000 LB/IN2 | D74 | 268% |
| Pet Balloon | 30000 LB/IN2 | M76 | 4% |
| Nylon Balloon | 15200 LB/IN2 | M72 | 120% |

[1]Elongation refers to the percentage increase in the length of the tubing prior to breaking. Brittle materials have a lower elongation relative to flexible materials.

The results in Table 2 show that balloons made of BAREX™, polyacrylonitrile, and of HYTREL™ were significantly softer (i.e., less hard) than the respective resins. Surprisingly, despite the increased softness, balloons made of HYTREL™ retained their tensile strength, and balloons made of polyacrylonitrile and of BAREX™ showed more than a two-fold increase in tensile strength compared to the respective resin. Similarly, BAREX™/HYTREL™ balloons were surprisingly both softer (i.e., had lower "hardness" value) and stronger (i.e., had a higher tensile strength) than either BAREX™ resins or HYTREL™ resin. These results were surprising since a decrease in hardness would have been expected to be associated with a decrease in tensile strength.

The results in Table 2 were also surprising because the increased tensile strength of the BAREX™/HYTREL™ balloons as compared to the individual component resins would have been expected to be associated with a decrease (or no change) in percent elongation.

The results in Table 2 also show that varying degrees of softness versus tensile strength can be tailor made by varying the components of the blend.

The ability of balloons manufactured using BAREX 210™, BAREX 218™, and acrylonitrile/HYTREL™ blend to resist pinholing, resist moisture, and bond to other materials was also compared using previously described methods (See e.g., Vishu Shah, *Handbook of Plastics Testing Technology*, John Wiley & Sons [1984]). The results are shown in Table 3.

TABLE 3

Comparison of Physical Properties of Balloons

| Material | Izod Impact Value[1] (ftlb/in) | Water Absorption[2] (% Absorp./ 24 hrs.) | Static Friction[3] (against polymer) |
|---|---|---|---|
| BAREX 210 ™ | 5.0 | .1–.2% | .35–.5 lbs |
| BAREX 218 ™ | 9.0 | .15–.25% | .35–.5 lbs |
| Acrylonitrile/HYTREL ™ 70/30 Blend | 3–4 | .08–.2% | .3–.5 lbs |
| Nylon 11 | 1.5 | .20–.40% | .15–.25 lbs |
| Nylon 12 | 1.2 | .5–1.2% | .1–.3 lbs |
| Polyester (TP) | 2.5 | .10–.20% | .15–.25 lbs |
| Polyethylene | 1.25 | .00–.01% | .10–.22 lbs |

[1]Izod Notched Impact Testing was done by ASTM D-638 by measuring impact/puncture resistance.
[2]Moisture Absorption Testing was done by ASTM D-570 by measuring resistance to moisture.
[3]Static Friction Testing was done by ASTM D-1894 by measuring polymer to polymer friction or ability to bond two materials.

The results in Table 3 show that the balloons manufactured out of "BAREX 210," "BAREX 218" and acrylonitrile/"HYTREL" (70/30) blend had a greater resistance to pinholing than any of the tested prior art balloons, and showed resistance to moisture as well as ability to bond to other materials.

EXAMPLE 3

Optimizing Balloon Preparation Conditions For Acrylonitrile Polymer Balloons And For Acrylonitrile-"HYTREL" Blend Balloons One of the desirable properties of a balloon catheter, especially stent placement catheters, is to be able to apply to the balloon a nominal pressure of from about 4 atmospheres to about 6 atmospheres without bursting the balloon. Another desirable property is that the catheter balloon has an even compliance curve so that the radial growth of the balloon under different pressures is predictable. In particular, it is desirable to obtain a quarter size growth of the balloon (i.e., an increase of 0.25 mm in the mean inside diameter of a balloon as compared to the mean nominal inside diameter (i.e., the inside diameter of the balloon while being subjected to pressure on its inner wall of from about 4 atmospheres to about 6 atmospheres) of the same balloon at a pressure from about 12 atmospheres to about 14 atmospheres. It is also desirable that the quarter size growth of the balloon be observed at a pressure which is at least 1–2 atmospheres below the rated burst pressure of the balloon in order to provide a safety margin when a stent is used. Quarter size growth is particularly important for stent placement since overinflation allows for securing the stent against the vessel wall without the risk of bursting.

Thus, this experiment was carried out in order to determine the conditions for producing a polyacrylonitrile balloon and a acrylonitrile/HYTREL™ blend balloon with a nominal pressure of from about 4 atmospheres to about 5 atmospheres, with quarter size growth from about 12 atmospheres to about 14 atmospheres, and with a rated burst pressure which is at least from about 1 atmospheres to about 2 atmospheres greater than the pressure at which quarter size growth is obtained.

Polyacrylonitrile balloons with a mean inside diameter of 2.5 mm, 3.0 mm, 3.5 mm and 4.0 mm, were fabricated as described in Example 1, with the exception that the tubing dimensions and balloon double wall dimensions were varied as shown in Tables 4–7 in order to produce the desired balloon mean inside diameter. The balloons were subjected to different amounts of pressure on their inside surface using pressurized fluid (e.g., distilled water) and the change in the mean outside diameter of the balloon was measured. The results are shown in Tables 4–7.

TABLE 4

Change Under Pressure In The Outside Diameter Of Polyacrylonitrile Balloons With A 2.5 mm Inside Diameter

EXTRUSION NUMBER

B-194-6[1]  B-194-5[2]  B-170-2  B-170-2  B-170-1  B-170-2  B-170-2
BALLOON DOUBLE WALL THICKNESS (.0013–.0015")
Outside Diameter of Balloon (Inches)[3]

| Pressure (psi) | MOLD SIZE | | | | MOLD SIZE | | |
|---|---|---|---|---|---|---|---|
| | 2.55 | 2.6 | | | 2.6 | 2.6 | 2.7 |
| 3 | 2.46 | 2.52 | 0.097 | 0.097 | 2.51 | 2.52 | 2.57 |
| 4 | 2.49 | 2.56 | 0.098 | 0.098 | 2.53 | 2.56 | 2.6 |
| 5 | 2.51 | 2.58 | 0.099 | 0.0985 | 2.55 | 2.58 | 2.63 |
| 6 | 2.52 | 2.6 | 0.0995 | 0.099 | 2.57 | 2.6 | 2.65 |
| 7 | 2.54 | 2.61 | 0.1 | 0.1 | 2.585 | 2.62 | 2.66 |

TABLE 4-continued

Change Under Pressure In The Outside Diameter Of Polyacrylonitrile Balloons With A 2.5 mm Inside Diameter

EXTRUSION NUMBER

| | B-194-6[1] | B-194-5[2] | B-170-2 | B-170-2 | B-170-1 | B-170-2 | B-170-2 |
|---|---|---|---|---|---|---|---|
| | BALLOON DOUBLE WALL THICKNESS (.0013–.0015") | | | | | | |
| | Outside Diameter of Balloon (Inches)[3] | | | | | | |
| Pressure | MOLD SIZE | | | | MOLD SIZE | | |
| (psi) | 2.55 | 2.6 | | | 2.6 | 2.6 | 2.7 |
| 8 | 2.56 | 2.63 | 0.1005 | 0.1005 | 2.605 | 2.63 | 2.68 |
| 9 | 2.57 | 2.65 | 0.101 | 0.101 | 2.62 | 2.65 | 2.69 |
| 10 | 2.58 | 2.67 | 0.1015 | 0.1015 | 2.63 | 2.66 | 2.71 |
| 11 | 2.595 | 2.69 | 0.102 | 0.102 | 2.64 | 2.68 | 2.72 |
| 12 | 2.605 | 2.71 | 0.1025 | 0.1025 | 2.655 | 2.71 | 2.74 |
| 13 | 2.62 | 2.75 | 0.103 | 0.103 | 2.67 | 2.73 | *2.75* |
| 14 | 2.64 | 2.78 | 0.1035 | 0.1035 | 2.7 | *2.75* | 2.77 |
| 15 | 2.66 | 2.81 | 0.1045 | 0.1045 | 2.715 | 2.77 | 2.79 |
| 16 | 2.68 | 2.85 | 0.1055 | 0.106 | 2.73 | 2.79 | 2.82 |
| 17 | 2.7 | 2.88 | 0.1065 | *0.1075* | *2.76* | 2.82 | 2.85 |
| 18 | 2.72 | 2.94 | *0.108* | 0.109 | 2.79 | 2.86 | 2.87 |
| 19 | *2.75* | 2.99 | 0.1095 | 0.111 | 2.845 | 2.9 | 2.9 |
| 20 | 2.78 | | 0.111 | 0.112 | 2.93 | 2.93 | 2.95 |
| 21 | 2.81 | | 0.113 | 0.115 | | 2.96 | 3 |
| 22 | 2.84 | | 0.115 | 0.117 | | | |
| Burst Avg. | 24.7 | 20.49 | 21.81 | 22.2 | 21.46 | 22.33 | 22.17 |
| S. Deviat. | 1.19 | 1.87 | 1.17 | 1.08 | 0.747 | 1.67 | 1.19 |
| Rated | 18.71 | 11.32 | 15.73 | 16.6 | 17.88 | 14.15 | 16.32 |
| Nominal | 4 | 2 | 4 | 4 | 3 | 2 | 2 |
| ¼ size | 19 | 13 | 18 | 17 | 17 | 14 | 13 |

[1]Tubing dimension is 0.14/.0365".
[2]Tubing dimension is 0.16/.041".
[3]Values highlighted in bold represent nominal outside diameter, values underlined represent quarter size outside diameter.

TABLE 5

Change Under Pressure In The Outside Diameter Of Polyacrylonitrile Balloons With A 3.0 mm Inside Diameter

EXTRUSION NUMBER

| | B-170-3 | B-194-B | B-200-3 | B-200-4 | B-194-3 | B-200-3 | B-200-3 | B-170-3 | B-170-3 | B-200-3 | B-200-3 |
|---|---|---|---|---|---|---|---|---|---|---|---|
| | BALLOON DOUBLE WALL THICKNESS (INCHES) | | | | | | | | | | |
| Pressure (psi) | .0013–.0015" | .0013–.0015" | .0013–.0015" | .0013–.0014" | .0013–.0015" | .0013–.0015" | .0010–.0011" | .0013–.0015" | .0013–.0015" | .0012–.0014" | .0010–.0010" |
| | OUTSIDE DIAMETER OF BALLOON (INCHES)[1] | | | | | | | | | | |
| 3 | 0.117 | 0.115 | 0.1155 | 0.1155 | 0.116 | 0.115 | 0.116 | 0.117 | 0.117 | 0.115 | 0.1165 |
| 4 | 0.118 | 0.117 | 0.117 | 0.117 | 0.117 | 0.116 | 0.118 | 0.118 | 0.118 | 0.117 | 0.118 |
| 5 | 0.119 | 0.118 | 0.118 | 0.118 | 0.118 | 0.118 | 0.119 | 0.119 | 0.119 | 0.1185 | 0.119 |
| 6 | 0.12 | 0.119 | 0.119 | 0.119 | 0.119 | 0.119 | 0.12 | 0.12 | 0.12 | 0.195 | 0.12 |
| 7 | 0.121 | 0.12 | 0.12 | 0.1195 | 0.12 | 0.1195 | 0.121 | 0.1205 | 0.1205 | 0.12 | 0.121 |
| 8 | 0.1215 | 0.12 | 0.121 | 0.12 | 0.1205 | 0.12 | 0.1225 | 0.121 | 0.121 | 0.1205 | 0.1225 |
| 9 | 0.122 | 0.121 | 0.1215 | 0.1212 | 0.121 | 0.121 | 0.1235 | 0.1215 | 0.1215 | 0.121 | 0.1235 |
| 10 | 0.1225 | 0.1215 | 0.122 | 0.1215 | 0.1215 | 0.1215 | 0.1245 | 0.122 | 0.1225 | 0.122 | 0.1245 |
| 11 | 0.123 | 0.122 | 0.1225 | 0.122 | 0.122 | 0.122 | 0.126 | 0.124 | 0.123 | 0.1225 | 0.126 |
| 12 | 0.124 | 0.1225 | 0.123 | 0.1225 | 0.123 | 0.1225 | *0.1275* | 0.1245 | 0.124 | 0.123 | 0.127 |
| 13 | 0.125 | 0.123 | 0.1235 | 0.123 | 0.1235 | 0.1235 | 0.1285 | 0.125 | 0.1245 | 0.1235 | *0.1285* |
| 14 | 0.1255 | 0.1235 | 0.1245 | 0.1235 | 0.124 | 0.1245 | 0.13 | 0.1255 | 0.1255 | 0.124 | 0.13 |
| 15 | 0.127 | 0.124 | 0.1255 | 0.124 | 0.1245 | 0.125 | 0.132 | 0.127 | 0.127 | 0.125 | 0.1315 |
| 16 | *0.128* | 0.125 | 0.126 | 0.125 | 0.125 | 0.1255 | 0.134 | *0.1285* | *0.1285* | 0.126 | 0.133 |
| 17 | 0.1295 | 0.126 | 0.127 | 0.126 | 0.1255 | *0.1275* | 0.137 | 0.13 | 0.13 | 0.1265 | 0.136 |
| 18 | 0.131 | *0.128* | *0.1285* | 0.127 | 0.126 | 0.129 | 0.14 | 0.132 | 0.132 | 0.127 | 0.139 |
| 19 | 0.133 | 0.129 | 0.1295 | *0.128* | *0.128* | 0.13 | 0.143 | 0.135 | 0.135 | *0.129* | |
| 20 | 0.136 | 0.13 | 0.1305 | 0.13 | 0.129 | 0.1315 | | 0.138 | 0.138 | 0.1305 | |
| 21 | 0.139 | 0.131 | 0.133 | 0.131 | | 0.133 | | 0.141 | 0.14 | 0.132 | |
| 22 | | 0.133 | 0.135 | 0.1325 | | | | | | 0.135 | |
| Burst Avg. | 20.3 | 19.9 | 23.5 | 23.7 | 17.2 | 22.3 | 18.3 | 21.3 | 21.3 | 21.5 | 17.9 |
| S. Deviat. | 0.86 | 1.91 | 0.907 | 0.536 | 3.2 | 0.624 | 0.938 | 0.76 | 0.82 | 0.535 | 0.98 |

TABLE 5-continued

Change Under Pressure In The Outside Diameter Of Polyacrylonitrile Balloons With A 3.0 mm Inside Diameter

EXTRUSION NUMBER

| Pressure (psi) | B-170-3 | B-194-B | B-200-3 | B-200-4 | B-194-3 | B-200-3 | B-200-3 | B-170-3 | B-170-3 | B-200-3 | B-200-3 |
|---|---|---|---|---|---|---|---|---|---|---|---|
| | .0013–.0015" | .0013–.0015" | .0013–.0015" | .0013–.0014" | .0013–.0015" | .0013–.0015" | .0010–.0011" | .0013–.0015" | .0013–.0015" | .0012–.0014" | .0010–.0010" |
| Rated | 15.83 | 5.5 | 16.7 | 0 | 19.7 | 19 | 12.6 | 17.3 | 17.2 | 17.96 | 12.8 |
| Nominal | 4 | 5 | 5 | 5 | 5 | 4 | 4 | 4 | 4 | 5 | 4 |
| ¼ size | 16 | 18 | 18 | 19 | 19 | 17 | 12 | 16 | 16 | 19 | 12.5 |

[1] Values highlighted in bold represent nominal outside diameter; values underlined represent quarter size outside diameter.

TABLE 6

Change Under Pressure in The Outside Diameter of Polyacrylonitrile Balloons With a 3.5 mm Inside Diameter

EXTRUSION NUMBER

| Pressure | B-200-5 | B-200-6 | B-200-6 | B-200-6 | B-200-7 | B-194-5 | B-194-4 | B-194-4 | B-204-1 |
|---|---|---|---|---|---|---|---|---|---|
| | .0013–.0015" | .0014–.0016" | .0014–.0016" | .0013–.0015" | .0014–.0016" | .0013–.0015" | .0010–.0012" | .0012–.0015" | .0013–.0015" |

OUTSIDE DIAMETER OF BALLOON AT PRESSURE IN INCHES

| Pressure | B-200-5 | B-200-6 | B-200-6 | B-200-6 | B-200-7 | B-194-5 | B-194-4 | B-194-4 | B-204-1 |
|---|---|---|---|---|---|---|---|---|---|
| 2 | 0.135 | 0.134 | 0.135 | 0.136 | 0.134 | 0.135 | 0.136 | | 0.134 |
| 3 | 0.136 | 0.136 | 0.136 | 0.137 | 0.135 | 0.137 | 0.138 | 0.135 | 0.1355 |
| 4 | 0.1375 | 0.138 | 0.137 | 0.138 | 0.136 | 0.138 | 0.1385 | 0.137 | 0.1375 |
| 5 | 0.139 | 0.139 | 0.138 | 0.139 | 0.138 | 0.139 | 0.14 | 0.1385 | 0.1385 |
| 6 | 0.14 | 0.14 | 0.139 | 0.14 | 0.139 | 0.14 | 0.141 | 0.14 | 0.1395 |
| 7 | 0.141 | 0.1405 | 0.14 | 0.141 | 0.1395 | 0.141 | 0.142 | 0.1415 | 0.1405 |
| 8 | 0.142 | 0.141 | 0.1405 | 0.142 | 0.1405 | 0.1415 | 0.1425 | 0.1415 | 0.141 |
| 9 | 0.1425 | 0.142 | 0.1415 | 0.143 | 0.141 | 0.142 | 0.1435 | 0.1425 | 0.142 |
| 10 | 0.143 | 0.1425 | 0.1425 | 0.1435 | 0.1415 | 0.143 | 0.144 | 0.144 | 0.143 |
| 11 | 0.144 | 0.143 | 0.143 | 0.144 | 0.142 | 0.1435 | 0.146 | 0.145 | 0.144 |
| 12 | 0.146 | 0.144 | 0.144 | 0.145 | 0.1435 | 0.1445 | 0.147 | 0.146 | 0.145 |
| 13 | 0.1465 | 0.1445 | 0.1445 | 0.146 | 0.144 | 0.1455 | <u>0.148</u> | <u>0.1475</u> | 0.146 |
| 14 | <u>0.1485</u> | 0.146 | 0.146 | 0.1465 | 0.145 | 0.1475 | 0.149 | 0.149 | <u>0.1485</u> |
| 15 | 0.1505 | 0.147 | 0.147 | <u>0.148</u> | 0.146 | <u>0.148</u> | 0.151 | 0.151 | 0.15 |
| 16 | 0.1525 | <u>0.148</u> | <u>0.148</u> | 0.1495 | 0.147 | 0.149 | 0.153 | 0.153 | 0.155 |
| 17 | 0.157 | 0.1495 | 0.1495 | 0.151 | <u>0.148</u> | 0.1515 | 0.156 | 0.156 | 0.16 |
| 18 | 0.1595 | 0.1515 | 0.151 | 0.153 | 0.149 | 0.153 | 0.158 | 0.158 | |
| 19 | | 0.153 | 0.1535 | 0.155 | 0.15 | 0.155 | 0.16 | 0.161 | |
| 20 | | 0.155 | 0.157 | 0.158 | 0.152 | 0.158 | | | |
| 21 | | | 0.159 | | 0.155 | | | | |
| 22 | | | | | 0.159 | | | | |
| Burst Avg. | 18.4 | 20.8 | 20.87 | 19.83 | 21.52 | 19.1 | 19 | 20 | 16.6 |
| S. Deviat. | 0.894 | 0.85 | 0.505 | 0.709 | 0.671 | 1.03 | 0.707 | 0.894 | 0.534 |
| Rated | 11.7 | 16.4 | 17.5 | 15.14 | 18.03 | 13.74 | 15 | 14.1 | 12.6 |
| Nominal | 5 | 4 | 5 | 4 | 5 | 4 | 3 | 5 | 5 |
| ¼ Size | 14 | 16 | 16 | 15 | 17 | 15 | 13 | 13 | 14 |

TABLE 7

Change Under Pressure In The Outside Diameter Of Polyacrylonitrile Balloons With A 4.0 mm Inside Diameter

EXTRUSION NUMBER

| Pressure | B-200-9 | B-200-8 | B-204-4 | B-204-2 | B-204-3 | B-204-1 | B-200-8 | B-200-9 |
|---|---|---|---|---|---|---|---|---|
| | .0011–.0013" | .0011–.0012" | .0008–.0010" | .0009–.0011" | .0008–.0009" | .0011–.0013" | .0011–.0012" | .0011–.0012" |
| 2 | 0.154 | 0.154 | 0.1545 | 0.1545 | 0.157 | 0.154 | | 0.155 |
| 3 | 0.156 | 0.156 | 0.1575 | 0.1565 | 0.158 | 0.156 | 0.156 | 0.156 |
| 4 | 0.157 | 0.1575 | 0.1615 | 0.158 | 0.1605 | 0.158 | 0.158 | 0.158 |
| 5 | 0.158 | 0.159 | 0.1645 | 0.16 | 0.163 | 0.159 | 0.159 | 0.159 |

TABLE 7-continued

Change Under Pressure In The Outside Diameter Of
Polyacrylonitrile Balloons With A 4.0 mm Inside Diameter

EXTRUSION NUMBER

| Pressure | B-200-9 .0011–.0013" | B-200-8 .0011–.0012" | B-204-4 .0008–.0010" | B-204-2 .0009–.0011" | B-204-3 .0008–.0009" | B-204-1 .0011–.0013" | B-200-8 .0011–.0012" | B-200-9 .0011–.0012" |
|---|---|---|---|---|---|---|---|---|
| | | | BALLOON DOUBLE WALL THICKNESS (INCHES)[1] | | | | | |
| 6 | 0.159 | 0.16 | <u>0.1695</u> | 0.162 | <u>0.167</u> | 0.1605 | 0.16 | 0.161 |
| 7 | 0.161 | 0.1615 | 0.176 | 0.164 | 0.172 | 0.1615 | 0.162 | 0.162 |
| 8 | 0.162 | 0.1625 | 0.1825 | 0.165 | 0.179 | 0.163 | 0.163 | 0.163 |
| 9 | 0.163 | 0.164 | 0.189 | 0.166 | 0.187 | 0.164 | 0.164 | 0.164 |
| 10 | 0.164 | 0.165 | | 0.168 | 0.194 | 0.166 | 0.165 | 0.165 |
| 11 | 0.165 | 0.166 | | 0.171 | | <u>0.168</u> | 0.166 | 0.166 |
| 12 | 0.166 | <u>0.169</u> | | 0.174 | | 0.17 | <u>0.168</u> | 0.167 |
| 13 | <u>0.167</u> | 0.171 | | 0.178 | | 0.173 | 0.17 | <u>0.168</u> |
| 14 | 0.169 | 0.173 | | 0.1835 | | 0.176 | 0.172 | 0.169 |
| 15 | 0.17 | 0.177 | | | | 0.184 | 0.175 | 0.17 |
| 16 | 0.172 | 0.179 | | | | | 0.177 | 0.172 |
| 17 | 0.174 | 0.18 | | | | | | 0.174 |
| 18 | 0.176 | 0.184 | | | | | | 0.178 |
| Burst Avg. | 16.4 | 17.8 | 9.68 | 11.67 | 10.76 | 13.35 | 16.74 | 18.9 |
| S. Deviate. | 1.07 | 0.88 | N/A | N/A | N/A | N/A | 1.36 | 0.78 |
| Rated | 10.8 | 13.2 | N/A | N/A | N/A | N/A | 9.68 | 14.84 |
| Nominal | 5 | 4.5 | 3 | 4 | 3 | 4 | 4 | 4 |
| ¼ Size | 14 | 12 | 6 | 10 | 6 | 11 | 12 | 13 |

Values highlighted in bold represent the nominal outside diameter; values underlined represent quarter size outside diameter The results in Tables 4–7 show that the conditions tested failed to produce a polyacrylonitrile balloon having a mean outside diameter of either 2.5 mm (Table 4) or 3.5 mm (Table 6) which had a nominal pressure of 4–5 atmospheres, quarter size growth from about 12 atmospheres to about 14 atmospheres, and a high rated burst pressure. Nevertheless, polyacrylonitrile balloons which had a mean outside diameter of 3.5 mm (Table 5) or 4.0 mm (Table 7) were successfully fabricated with a nominal pressure of 4–5 atmospheres, quarter size growth at from 12 to 14 atmospheres, and a high rated burst pressure.

Acrylonitrile/HYTREL™ blend balloons containing from 60/40 to 80/20 acrylonitrile/HYTREL™ by weight, and with a mean outside diameter of 2.0, 2.5 mm, 3.0 mm, and 3.5 mm, were fabricated as described in Example 1, with the exception that the tubing dimensions and balloon double wall dimensions were varied in order to produce the desired balloon mean outside diameter. The balloons were subjected to different amounts of internal pressure using pressurized fluid (e.g., distilled water) and the change in the outside diameter of the balloon was measured. The results are shown in Table 8.

TABLE 8

Change Under Pressure In The Outside Diameter Of Acrylonitrile/HYTREL™ Blend Balloons

| Material | Average Burst Press. (atm) | Std. Dev. (atm) | Rated Burst Press. (atm) | ¼ Size Pressure | Nominal Pressure | D.W.T |
|---|---|---|---|---|---|---|
| 3.5 MM | | | | | | |
| 80/20 (1) | 25.3 | 0.579 | 22.98 | 17 | 8 | 0.0014 |
| 70/30 (1) | 21.3 | 2.89 | 9.74 | 14.5 | 7 | 0.0014 |
| 70/30 (2) | 18.8 | 2.6 | 8.4 | 14.5 | 4 | 0.0011 |
| 60/40 (1) | 18 | 1.73 | 11.07 | 13 | 6 | 0.0013 |
| 60/40 (2) | 17.6 | 1.14 | 13.04 | 13 | 4 | 0.0011 |
| 3.0 MM | | | | | | |
| 80/20 (1) | 24.7 | 0.579 | 22.38 | 17 | 8 | 0.0014 |
| 70/30 (1) | 25 | 0 | 25 | 15.5 | 9 | 0.0014 |
| 70/30 (2) | 23.4 | 0.548 | 21.2 | 18.5 | 4 | 0.0014 |
| 60/40 (1) | 26.7 | 1.15 | 22.08 | 16 | 9 | 0.0014 |
| 60/40 (2) | 20.2 | 1.3 | 15 | 14.5 | 4 | 0.0014 |
| 2.5 MM | | | | | | |
| 70/30 | 24.2 | 0.84 | 20.84 | 14 | 4 | 0.0014 |
| 60/40 | 24 | 1.22 | 19.12 | 13 | 4 | 0.0014 |

TABLE 8-continued

Change Under Pressure In The Outside Diameter Of Acrylonitrile/HYTREL ™ Blend Balloons

| Material | Average Burst Press. (atm) | Std. Dev. (atm) | Rated Burst Press. (atm) | ¼ Size Pressure | Nominal Pressure | D.W.T |
|---|---|---|---|---|---|---|
| 2.0 MM | | | | | | |
| 70/30 | 27.4 | 1.34 | 22.04 | 20.5 | 4 | 0.0014 |
| 60/40 | 25 | 0 | 25 | 17.5 | 4 | 0.0014 |

The results in Table 8 show that the conditions tested failed to produce an acrylonitrile/HYTREL™ blend balloon with a mean outside diameter of either 2.0 mm or 3.0 mm, and with a nominal pressure of. 4–5 atmospheres, quarter size growth at a pressure from 12–14 atmospheres, and a high rated burst pressure. However, Table 8 demonstrates that acrylonitrile/"HYTREL" blend balloons which had a mean outside diameter of 2.5 mm or 3.5 mm, and which also had a nominal pressure of 4–5 atmospheres, quarter size growth at a pressure from 12–14 atmospheres, and a high rated burst pressure were successfully fabricated.

EXAMPLE 4

Comparative Compliance, Burst Pressure, And Quarter Size Growth Of Balloons Fabricated Of Polyacrylonitrile, Low Density Polyethylene, Polyethylene And Nylon This experiment was carried out to compare the properties of polyacrylonitrile catheter balloons to compliant, non-compliant, and semi-compliant balloons. In the following experiments, unless otherwise mentioned, an 3.0×20 mm (i.e., 3.0 mm mean outside diameter and 20 mm in length) polyacrylonitrile balloon with a double wall thickness of 0.0007 inches which was fabricated as described in Example 1 was used.

A. Compliance And Rupture Pressure

The tailored compliance of polyacrylonitrile balloons prepared as described in Example 1 was compared to the tailored compliance of biaxially oriented 3.0 mm×20 mm semi-compliant nylon balloons with a wall thickness of 0.0010–0.0012 inches, compliant highly irradiated linear low density polyethylene (LDPE) balloons with a wall thickness of 0.0014–0.0015 inches, and non-compliant crosslinked low density polyethylene (PET) balloons with a wall thickness of 0.0007–0.0008 inches. The results are shown in FIG. 1.

FIG. 1 shows that the polyacrylonitrile balloon exhibits a tailored compliance of less than 13% at below 200 psi and less than 7% at pressures greater than 200 psi (i.e., about 13.6 atmospheres). FIG. 1 also shows that the tailored compliance of the polyacrylonitrile balloon was greater than the tailored compliance of the non-compliant PET balloons at every pressure tested, and was similar at pressures below about 9 atmospheres to the tailored compliance of compliant LDPE balloons and of semi-compliant nylon balloons. FIG. 1 further shows that the tailored compliance of the polyacrylonitrile balloon at pressures greater than 9 atmospheres was intermediate between that of compliant and non-compliant balloons. Significantly, compliance of the polyacrylonitrile balloon above 9 atmospheres was linear, thus providing a predictable distension at a given pressure.

The rated burst pressure of 3.0 mm mean outside diameter balloons was also determined and found to be 16–18 atm for non-compliant PET balloons, 10–14 atm for semi-compliant nylon balloons, 8–10 atm for compliant LDPE balloons, and 14–16 atm for polyacrylonitrile balloons. These results demonstrate that polyacrylonitrile balloons exhibit a higher rated burst pressure than compliant LDPE balloons, with a rated burst pressure which is comparable to that of non-compliant PET balloons.

The results discussed above demonstrate the superior combination of tailored compliance and of rated burst pressure of polyacrylonitrile balloons, in that polyacrylonitrile balloons exhibited relatively high burst pressure (similar to non-compliant PET balloons) while also exhibiting relatively high tailored compliance (similar to semi-compliant nylon balloons and greater than non-compliant PET balloons).

B. Nominal Size And Quarter Size Growth From 12 To 14 Atmospheres

The nominal size and quarter size growth of 3.0 mm balloons constructed of polyacrylonitrile (as described supra, Example 1), nylon, LDPE and PET was compared to determine whether a nominal mean outside diameter of 3.0 could be obtained at a pressure from about 4 to about 6 atm, and whether quarter size growth could be obtained at a pressure of from about 12 atm to about 14 atm. The results are shown in Table 9.

TABLE 9

Change in The Outside Diameter of Balloons Under Pressure

| PRESSURE (ATM) | OUTSIDE DIAMETER (INCHES) | | | |
|---|---|---|---|---|
| | PET | NYLON | ACRYLONITRILE | LDPE |
| 4 | 2.99 | 2.92 | 2.95 | 2.95 |
| 5 | 2.99 | 2.95 | 3 | 3 |
| 6 | 3 | 3 | 3.03 | 3.05 |
| 7 | 3 | 3.05 | 3.06 | 3.1 |
| 8 | 3.05 | 3.09 | 3.09 | 3.15 |
| 9 | 3.05 | 3.14 | 3.12 | 3.2 |
| 10 | 3.07 | 3.18 | 3.15 | 3.25 |
| 11 | 3.08 | 3.22 | 3.18 | 3.3 |
| 12 | 3.09 | 3.26 | 3.22 | 3.35 |
| 13 | 3.09 | 3.32 | 3.25 | 3.42 |
| 14 | 3.1 | 3.38 | 3.28 | 3.5 |
| 15 | 3.1 | 3.45 | 3.30 | 3.6 |
| 16 | 3.11 | 3.52 | 3.32 | 3.74 |
| 17 | 3.11 | 3.59 | 3.34 | 3.83 |
| 18 | 3.12 | 3.67 | 3.36 | 3.92 |
| 19 | 3.12 | 3.74 | 3.39 | 4 |
| 20 | 3.13 | 3.82 | 3.42 | 4.12 |

[1]Values highlighted in bold represent quarter size outside diameter.

Table 9 shows that each of the balloons tested achieved nominal size at a pressure from 4–6 atm. The results in Table 9 also show that only nylon balloons and polyacrylonitrile balloons reached quarter size at a pressure from 12–14 atm. In contrast, LDPE balloons were more compliant than polyacrylonitrile balloons, thus reaching quarter size at pressures below 12 atm, while PET balloons were less compliant than polyacrylonitrile balloons and did not reach quarter size even at a pressure of as high as 20 atm.

These results demonstrate that, in addition to their combined properties of higher compliance as compared to non-compliant balloons and of higher rated burst pressure as compared to compliant balloons, polyacrylonitrile balloons also exhibit the property of reaching quarter size at a pressure from 12–14 atm, and reaching nominal size at a pressure from 4–6 atm.

EXAMPLE 5

Compliance of Biaxially Oriented Acrylonitrile-"HYTREL" Blend Balloons

Figure 2:
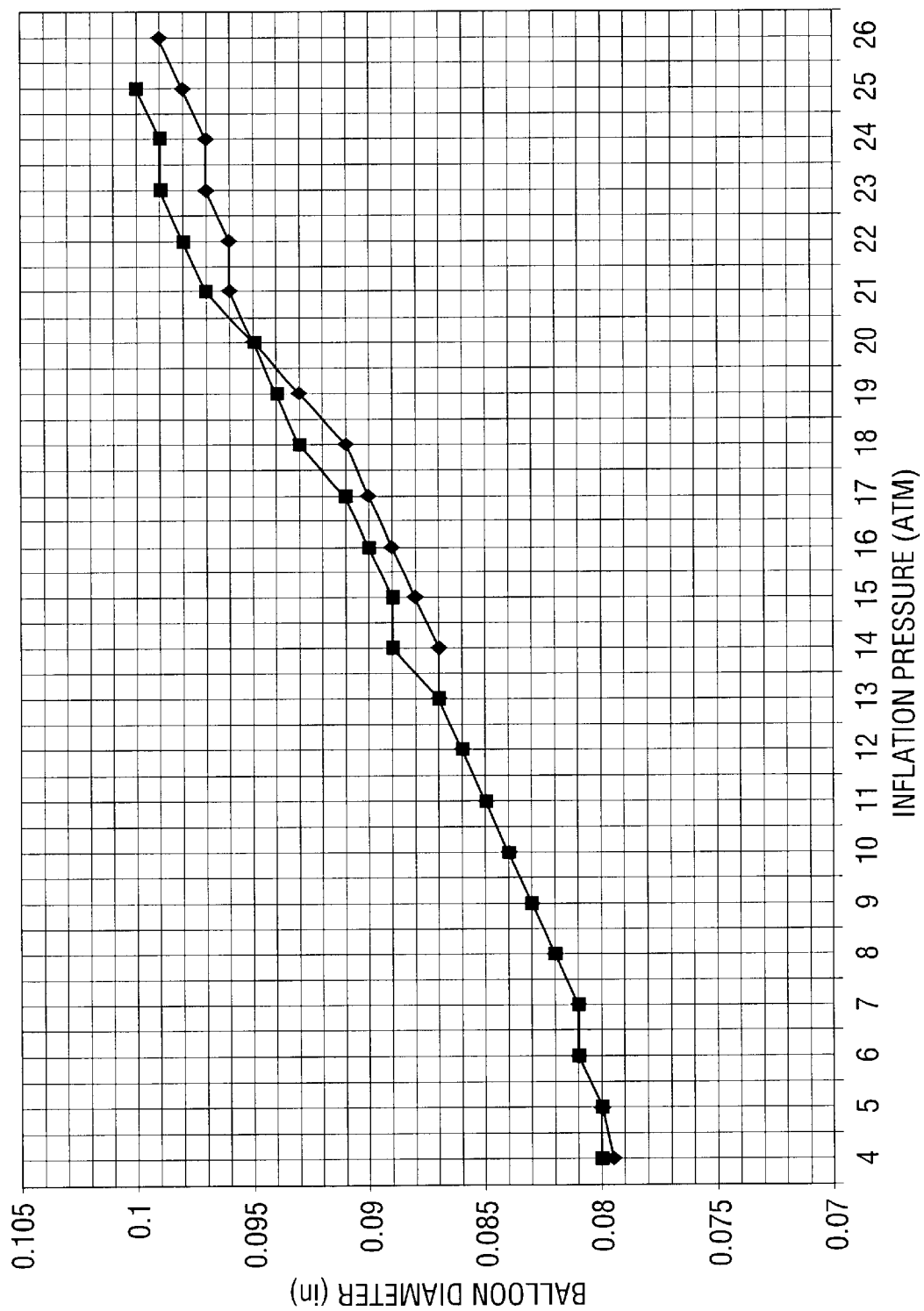
FIG. 2 shows the change in the out side diameter, in response to pressure, of 2.0 mm balloons fabricated of acrylonitrile/HYTREL™ 70/30 bend (♦) and 60/40 blend (■).
Figure 3:
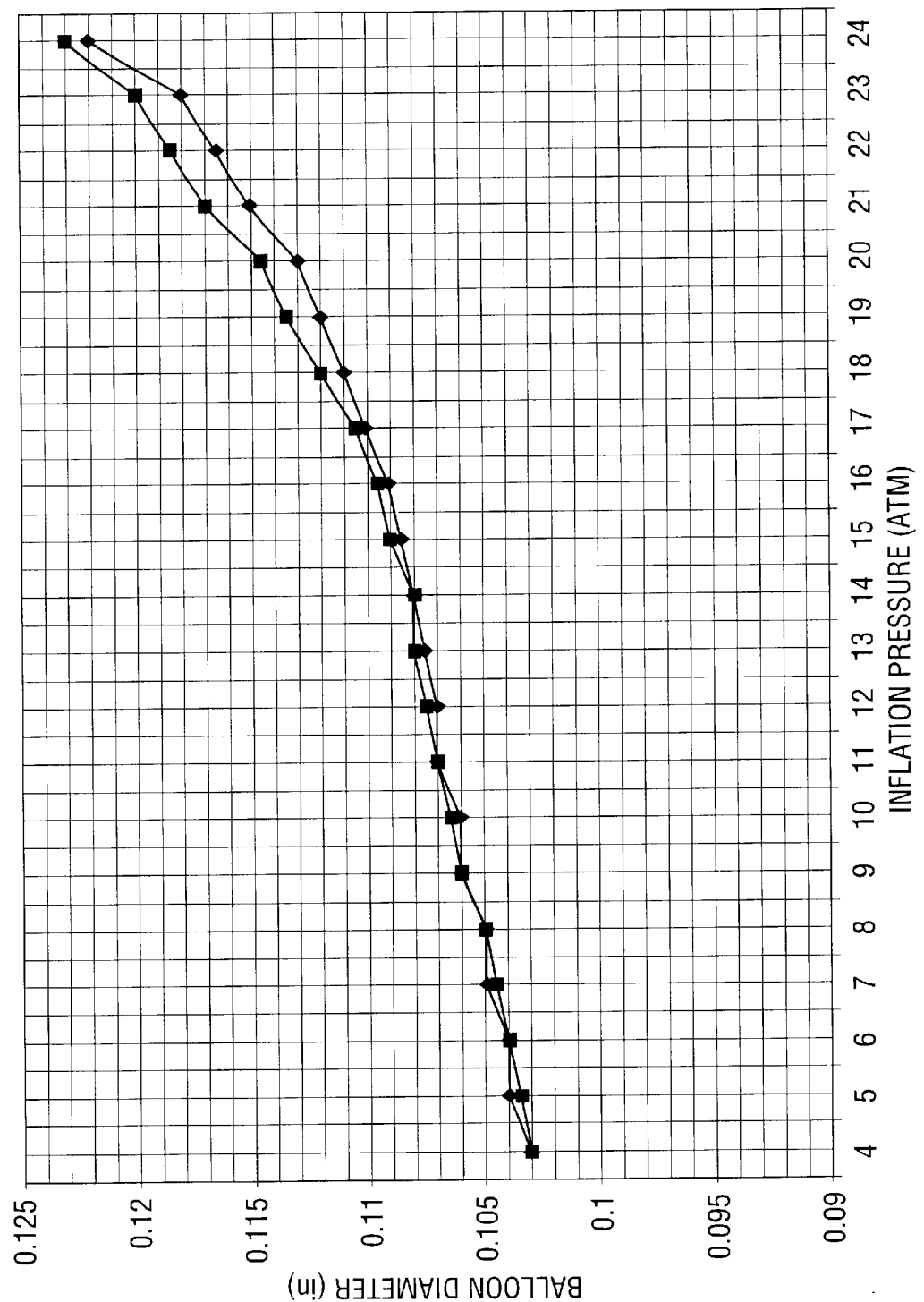
FIG. 3 shows the change in the outside diameter, in response to pressure, of 2.5 mm balloons fabricated of acrylonitrile/HYTREL™ 70/30 blend (♦) and 60/40 blend (■).

Tailored compliance of 2.0 mm and 2.5 mm balloons with a double wall thickness of acrylonitrile/HYTREL™ blend was determined and the results are shown in FIGS. 2 and 3. The results in FIGS. 2 and 3 show that acrylonitrile-HYTREL™ blend balloons containing different proportions of HYTREL™ exhibit different compliance curves. In particular, significant differences in compliance between balloons containing different proportions of HYTREL™ were observed at a pressure of about at least about 14 atmospheres (about 200 psi). For example, the tailored compliance of the acrylonitrile/HYTREL™ 60/40 blend and 70/30 blend balloons above 18 atmospheres was about 0.0020 inches/atmosphere and 0.0015 inches/atmosphere, respectively. These results suggest that balloon compliance may be tailored by varying the proportion of its components.

From the above data it is clear that the present invention provides catheter balloons having relatively high tensile strength, controlled compliance, reduced tendency for pinholing, ease of coating with and of bonding to other compounds, as well as resistance to moisture.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

What is claimed is:

1. A catheter balloon consisting of biaxially oriented acrylonitrile homopolymer.

2. The catheter balloon of claim 1, wherein said balloon is within its glass transition state at approximately human body temperature.

3. The catheter balloon of claim 1, wherein said acrylonitrile polymer catheter balloon has a mean wall thickness of from approximately 0.0006 inches to approximately 0.0013 inches and a tensile strength of at least approximately 15000 psi.

4. The catheter balloon of claim 3, wherein said balloon has tailored compliance from approximately 5% to approximately 15%.

5. The catheter balloon of claim 1, wherein said acrylonitrile polymer catheter balloon has a mean wall thickness of from approximately 0.0006 inches to approximately 0.0015 inches, reaches approximately quarter size at a pressure from approximately 12 atmospheres to approximately 14 atmospheres, reaches nominal size at a pressure of from approximately 4 atmospheres to approximately 6 atmospheres, and has a rated burst pressure of at least approximately 1 atmosphere greater than said pressure from approximately 12 atmospheres to approximately 14 atmospheres.

6. A single-layer catheter balloon consisting of biaxially oriented acrylonitrile copolymer, wherein said acrylonitrile copolymer comprises acrylonitrile and methyl acrylate.

7. The catheter balloon of claim 6, wherein said acrylonitrile copolymer comprises from approximately 73 to approximately 77 parts by weight of acrylonitrile and from approximately 23 to approximately 27 parts by weight of methyl acrylate.

8. The catheter balloon of claim 7, wherein said balloon has a mean wall thickness of from approximately 0.0006 inches to approximately 0.0012 inches and a tensile strength of at least approximately 15000 psi.

9. The catheter balloon of claim 8, wherein said balloon has tailored compliance of from approximately 5% to approximately 15%.

10. The catheter balloon of claim 9, wherein said balloon has intrinsic viscosity from approximately 0.8 to approximately 1.3.

11. The catheter balloon of claim 6, wherein said acrylonitrile and methyl acrylate copolymer catheter balloon has a mean wall thickness of from approximately 0.0006 inches to approximately 0.0012 inches, reaches approximately quarter size at a pressure from approximately 12 atmospheres to approximately 14 atmospheres, reaches nominal size at a pressure of from approximately 4 atmospheres to approximately 6 atmospheres, and has a rated burst pressure of at least approximately 1 atmosphere greater than said pressure from approximately 12 atmospheres to approximately 14 atmospheres.

12. A single-layer catheter balloon consisting of biaxially oriented acrylonitrile copolymer, wherein said acrylonitrile copolymer comprises from approximately 73 to approximately 77 parts by weight of acrylonitrile and from approximately 23 to approximately 27 parts by weight of methyl acrylate.

13. The catheter balloon of claim 12, wherein said catheter balloon has a mean wall thickness of from approximately 0.0006 inches to approximately 0.0013 inches and a tensile strength of at least approximately 15000 psi.

14. The catheter balloon of claim 13, wherein said balloon has tailored compliance of from approximately 5% to approximately 15%.

15. The catheter balloon of claim 14, wherein said balloon has intrinsic viscosity from approximately 0.8 to approximately 1.3.

16. The catheter balloon of claim 13, wherein said catheter balloon has a mean wall thickness of from approximately 0.0006 inches to approximately 0.0013 inches, reaches approximately quarter size at a pressure from approximately 12 atmospheres to approximately 14 atmospheres, reaches nominal size at a pressure of from approximately 4 atmospheres to approximately 6 atmospheres, and has a rated burst pressure of at least approximately 1 atmosphere greater than said pressure from approximately 12 atmospheres to approximately 14 atmospheres.

17. A single-layer catheter balloon consisting of biaxially oriented acrylonitrile copolymer, wherein said acrylonitrile copolymer is thermoplastic, and wherein said acrylonitrile copolymer comprises acrylonitrile and methyl acrylate.

18. The catheter balloon of claim 17, wherein said acrylonitrile copolymer comprises from approximately 73 to approximately 77 parts by weight of acrylonitrile and from approximately 23 to approximately 27 parts by weight of methyl acrylate.

19. The catheter balloon of claim 18, wherein said balloon has a mean wall thickness of from approximately 0.0006 inches to approximately 0.0012 inches and a tensile strength of at least approximately 15000 psi.

20. The catheter balloon of claim 19, wherein said balloon has tailored compliance of from approximately 5% to approximately 15%.

21. The catheter balloon of claim 20, wherein said balloon has intrinsic viscosity from approximately 0.8 to approximately 1.3.

22. The catheter balloon of claim 17, wherein said acrylonitrile and methyl acrylate copolymer catheter balloon has a mean wall thickness of from approximately 0.0006 inches to approximately 0.0012 inches, reaches approximately quarter size at a pressure from approximately 12 atmospheres to approximately 14 atmospheres, reaches nominal size at a pressure of from approximately 4 atmospheres to approximately 6 atmospheres, and has a rated burst pressure of at least approximately 1 atmosphere greater than said pressure from approximately 12 atmospheres to approximately 14 atmospheres.

23. A single-layer catheter balloon consisting of biaxially oriented acrylonitrile copolymer, wherein said acrylonitrile copolymer is thermoplastic, and wherein said acrylonitrile copolymer comprises from approximately 73 to approximately 77 parts by weight of acrylonitrile and from approximately 23 to approximately 27 parts by weight of methyl acrylate.

24. The catheter balloon of claim 23, wherein said catheter balloon has a mean wall thickness of from approximately 0.0006 inches to approximately 0.0013 inches and a tensile strength of at least approximately 15000 psi.

25. The catheter balloon of claim 24, wherein said balloon has tailored compliance of from approximately 5% to approximately 15%.

26. The catheter balloon of claim 25, wherein said balloon has intrinsic viscosity from approximately 0.8 to approximately 1.3.

27. The catheter balloon of claim 23, wherein said catheter balloon has a mean wall thickness of from approximately 0.0006 inches to approximately 0.0013 inches, reaches approximately quarter size at a pressure from approximately 12 atmospheres to approximately 14 atmospheres, reaches nominal size at a pressure of from approximately 4 atmospheres to approximately 6 atmospheres, and has a rated burst pressure of at least approximately 1 atmosphere greater than said pressure from approximately 12 atmospheres to approximately 14 atmospheres.

28. A catheter balloon consisting of biaxially oriented acrylonitrile blend.

29. A catheter balloon consisting of biaxially oriented acrylonitrile blend, wherein said acrylonitrile blend comprises acrylonitrile and polyethylene elastomer.

30. The catheter balloon of claim 29, wherein said acrylonitrile blend comprises approximately 70 parts by weight of acrylonitrile and approximately 30 parts by weight of polyethylene elastomer.

31. The catheter balloon of claim 29, wherein said catheter balloon has a mean wall thickness of from approximately 0.00065 inches to approximately 0.0015 inches and a tensile strength of at least approximately 15000 psi.

32. The catheter balloon of claim 29, wherein said balloon has tailored compliance from approximately 5% to approximately 15%.

33. The catheter balloon of claim 29, wherein said balloon has intrinsic viscosity from approximately 0.8 to approximately 1.3.

34. The catheter balloon of claim 29, wherein said acrylonitrile and polyethylene elastomer blend catheter balloon has a mean wall thickness of from approximately 0.0006 inches to approximately 0.0012 inches, reaches approximately quarter size at a pressure from approximately 12 atmospheres to approximately 14 atmospheres, reaches nominal size at a pressure of from approximately 4 atmospheres to approximately 6 atmospheres, and has a rated burst pressure of at least approximately 1 atmosphere greater than said pressure from approximately 12 atmospheres to approximately 14 atmospheres.

35. A catheter balloon comprising biaxially oriented acrylonitrile blend, wherein said acrylonitrile blend comprises acrylonitrile and a block copolymer comprising crystalline polybutylene terephthalate and amorphous long chain glycols.

36. The catheter balloon of claim 35, wherein said acrylonitrile blend comprises approximately 70 parts by weight of acrylonitrile and approximately 30 parts by weight of said block copolymer.

37. The catheter balloon of claim 35, wherein said catheter balloon has a mean wall thickness of from approximately 0.0006 inches to approximately 0.0013 inches and a tensile strength of at least approximately 15000 psi.

38. The catheter balloon of claim 35, wherein said balloon has tailored compliance from approximately 5% to approximately 15%.

39. The catheter balloon of claim 35, wherein said balloon has intrinsic viscosity from approximately 0.8 to approximately 1.3.

40. The catheter balloon of claim 35, wherein said balloon has a mean wall thickness of from approximately 0.0006 inches to approximately 0.0013 inches, reaches approximately quarter size at a pressure from approximately 12 atmospheres to approximately 14 atmospheres, reaches nominal size at a pressure of from approximately 4 atmospheres to approximately 6 atmospheres, and has a rated burst pressure of at least approximately 1 atmosphere greater than said pressure from approximately 12 atmospheres to approximately 14 atmospheres.

41. A catheter balloon consisting of biaxially oriented acrylonitrile blend, wherein said acrylonitrile blend comprises acrylonitrile and polyether block amide.

42. The catheter balloon of claim 41, wherein said acrylonitrile blend comprises approximately 60 parts by weight of acrylonitrile and approximately 40 parts by weight of polyether block amide.

43. The catheter balloon of claim 41, wherein said acrylonitrile and polyether block amide blend catheter balloon has a mean wall thickness of from approximately 0.0006 inches to approximately 0.0013 inches and a tensile strength of at least approximately 15000 psi.

44. The catheter balloon of claim 41, wherein said balloon has tailored compliance from approximately 5% to approximately 15%.

45. The catheter balloon of claim 41, wherein said balloon has intrinsic viscosity from approximately 0.8 to and approximately 1.3.

46. The catheter balloon of claim 41, wherein said acrylonitrile and polyether block amide blend catheter balloon has intrinsic viscosity from approximately 0.8 to and approximately 1.3, a mean wall thickness of from approximately 0.0006 inches to approximately 0.0013 inches, reaches approximately quarter size at a pressure from approximately 12 atmospheres to approximately 14 atmospheres, reaches nominal size at a pressure of from approximately 4 atmospheres to approximately 6 atmospheres, and has a rated burst pressure of at least approximately 1 atmosphere greater than said pressure from approximately 12 atmospheres to approximately 14 atmospheres.

47. A single-layer catheter balloon comprising biaxially oriented acrylonitrile copolymer, wherein said acrylonitrile copolymer comprises acrylonitrile and methyl acrylate.

* * * * *